US009464997B2

(12) United States Patent
Li et al.

(10) Patent No.: US 9,464,997 B2
(45) Date of Patent: Oct. 11, 2016

(54) METHODS AND APPARATUSES FOR MEASURING EFFECTIVE ATOMIC NUMBER OF AN OBJECT

(71) Applicants: Nuctech Company Limited, Beijing (CN); Tsinghua University, Beijing (CN)

(72) Inventors: Shuwei Li, Beijing (CN); Zhiqiang Chen, Beijing (CN); Yuanjing Li, Beijing (CN); Ziran Zhao, Beijing (CN); Yinong Liu, Beijing (CN); Qingjun Zhang, Beijing (CN); Weibin Zhu, Beijing (CN); Yi Wang, Beijing (CN); Shuqing Zhao, Beijing (CN); Wenjian Zhang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 94 days.

(21) Appl. No.: 14/129,669

(22) PCT Filed: Dec. 28, 2012

(86) PCT No.: PCT/CN2012/087849
§ 371 (c)(1),
(2) Date: Dec. 27, 2013

(87) PCT Pub. No.: WO2013/097768
PCT Pub. Date: Jul. 4, 2013

(65) Prior Publication Data
US 2014/0314201 A1 Oct. 23, 2014

(30) Foreign Application Priority Data

Dec. 30, 2011 (CN) .......................... 2011 1 0457151

(51) Int. Cl.
*G01N 23/087* (2006.01)
*G01T 1/22* (2006.01)

(52) U.S. Cl.
CPC ............... *G01N 23/087* (2013.01); *G01T 1/22* (2013.01); *G01N 2223/402* (2013.01); *G01N 2223/507* (2013.01)

(58) Field of Classification Search
CPC ............................... G01N 23/087; G01T 1/22
USPC .......... 378/57, 98.8, 98.9, 98.11; 250/370.09
See application file for complete search history.

(56) References Cited

U.S. PATENT DOCUMENTS

| | | | | |
|---|---|---|---|---|
| 4,851,687 A | * | 7/1989 | Ettinger et al. | ........... 250/390.04 |
| 5,087,818 A | * | 2/1992 | Bellian | ..................... G01T 1/22 |
| | | | | 250/361 R |

(Continued)

FOREIGN PATENT DOCUMENTS

| | | |
|---|---|---|
| CN | 101598799 A | 12/2009 |
| CN | 101629917 A | 1/2010 |

(Continued)

OTHER PUBLICATIONS

International Search Report and Written Opinion for PCT Application No. PCT/CN2012/087849, dated Apr. 18, 2013, 9 pages.

(Continued)

*Primary Examiner* — Allen C. Ho
(74) *Attorney, Agent, or Firm* — Westman, Champlin & Koehler, P.A.

(57) ABSTRACT

Methods and apparatuses for measuring an effective atomic number of an object are disclosed. The apparatus includes: a ray source configured to product a first X-ray beam having a first energy and a second X-ray beam having a second energy; a Cherenkov detector configured to receive the first X-ray beam and the second X-ray beam that pass through an object under detection, and to generate a first detection value and a second detection value; and a data processing device configured to obtain an effective atomic number of the object based on the first detection value and the second detection value. The Cherenkov detector can eliminate disturbance of X-rays below certain energy threshold with respect to the object identification, and thus accuracy can be improved for object identification.

8 Claims, 3 Drawing Sheets

(56) References Cited

U.S. PATENT DOCUMENTS

| | | | | |
|---|---|---|---|---|
| 5,153,438 | A * | 10/1992 | Kingsley | G01T 1/2018 250/370.09 |
| 5,559,324 | A * | 9/1996 | Rapkin | G01T 7/02 250/252.1 |
| 6,507,025 | B1 * | 1/2003 | Verbinski | G01V 5/0016 250/358.1 |
| 6,552,347 | B1 | 4/2003 | Dimcovski | |
| 6,713,765 | B2 * | 3/2004 | Testardi | A61N 5/1048 250/363.01 |
| 6,828,575 | B2 | 12/2004 | Luo et al. | |
| 7,039,159 | B2 * | 5/2006 | Muenchau | G01V 5/0016 378/57 |
| 7,045,787 | B1 * | 5/2006 | Verbinski | G01N 23/02 250/358.1 |
| 7,166,844 | B1 * | 1/2007 | Gormley | G01V 5/0016 250/358.1 |
| 7,297,914 | B2 * | 11/2007 | Pang | G01T 1/22 250/207 |
| 7,453,987 | B1 * | 11/2008 | Richardson | 378/98.9 |
| 7,683,335 | B2 * | 3/2010 | Treadwell | G01T 1/22 250/361 R |
| 7,897,925 | B2 * | 3/2011 | Goldberg | G01T 1/2935 250/251 |
| 8,457,274 | B2 * | 6/2013 | Arodzero et al. | 378/57 |
| 2010/0265078 | A1 * | 10/2010 | Friedman | G01T 1/26 340/600 |
| 2011/0163236 | A1 * | 7/2011 | Arodzero | 250/361 R |
| 2013/0136230 | A1 * | 5/2013 | Arodzero et al. | 378/57 |

FOREIGN PATENT DOCUMENTS

| | | |
|---|---|---|
| CN | 202393720 U | 8/2012 |
| JP | 06-294871 A | 10/1994 |
| JP | 10-221457 A | 8/1998 |
| JP | 2007-178329 A | 7/2007 |
| WO | 2011/117316 A2 | 9/2011 |

OTHER PUBLICATIONS

Li, Shuwei, "Employing Cerenkov Detection in Material Effective Material Atomic Number Detection of Dual-energy X-ray Beams", Nuclear Electronics & Detection Technology, Aug. 2010, vol. 30, No. 8, pp. 1012-1015, 4 total pages.

Wang, Zhigang et al., "Nuclear Counter Effect of Silicon Photodiode Used in CsI(Tl) Crystal Calorimeter", High Energy Physics and Nuclear Physics, Sep. 2006, vol. 30, No. 9, pp. 876-879, 4 total pages.

Ueno, K. et al., "Detection of minimum-ionizing particles and nuclear counter effect with pure BGO and BSO crystals with photodiode readout", Nucl. Instr. and Meth. In Phys. Rev. A, 1997, vol. 396, pp. 103-109, 18 total pages.

Satpathy, A. et al., "Nuclear counter effect of silicon PIN photodiode used in CsI(Tl) calorimeter", Nucl. Instr. and Meth. In Phys. Rev. A, 1997, vol. 391, pp. 423-426, 4 total pages.

Office Action for Canadian Patent Application No. 2,861,694, dated Aug. 17, 2015, 4 pages.

First Office Action, including Search Report, for Chinese Patent Application No. 201110457151.6, dated Jul. 29, 2014, 8 pages.

First Office Action for Japanese Patent Application No. 2014-516186, dated Jan. 6, 2015, 3 pages.

Second Office Action for Chinese Patent Application No. 201110457151.6, dated May 25, 2015, 3 pages.

Patent Examination Report No. 1 for Australian Patent Application No. 2012361427, dated Aug. 28, 2014, 3 pages.

Second Office Action for Japanese Patent Application No. 2014-516186, dated Jun. 9, 2015, 3 pages.

Bonazzola, G.C. et al., "A Precision Fast Dosimeter for Pulsed High Energy X-Ray Beams", Nuclear Instruments and Methods 176 (1980) 513-519, North-Holland Publishing Company, received Apr. 21, 1980, 8 pages.

Li, Shu-Wei et al., "Employing a Cerenkov detector for the thickness measurement of X-rays in a scattering background", CPC(HEP & NP), 2010, 34(12): 1895-1899, Chinese Physics C, vol. 34, No. 12, Dec. 2010, 5 pages.

Li, Shu-Wei et al., "Employing Cerenkov Detectors in Material Effective Material Atomic Number Detection of Dual-energy X-ray energy X-ray Beams", Nuclear Electronics & Detection Technology, vol. 30, No. 8, 1012-1015, 4 pages,Aug. 2010.

Li, Shu-Wei et al., "Monitoring the energy variation of an electron linac using a Cerenkov detector", CPC(HEP & NP), 2010, 34(1): 126-130, Chinese Physics C, vol. 34, No. 1, Jan. 2010, 5 pages.

Wang, Zhi-Gang et al., "Nuclear Counter Effect of Silicon Photodiode Used in CsI(TI) Crystal Calorimeter", High Energy Physics and Nuclear Physics, vol. 30, No. 9, Sep. 2006, 4 pages.

Li, Qingua et al., "Overlapped objects discrimination using dual-energy, high energy X-ray imaging", Tsinghua University (Sci & Tech), 2008, vol. 48, No. 8, 1256-1259, 4 pages.

* cited by examiner

METHODS AND APPARATUSES FOR MEASURING EFFECTIVE ATOMIC NUMBER OF AN OBJECT

CROSS-REFERENCE TO RELATED APPLICATION

This Application is a Section 371 National Stage Application of International Application No. PCT/CN2012/087849, filed 28 Dec. 2012 and published as WO 2013/097768 A1 on 4 Jul. 2013, the contents of which are hereby incorporated by reference in their entirety.

TECHNICAL FIELD

The present application relates to security inspection, and particularly to methods and apparatuses for measuring an effective atomic number ($Z_{eff}$) of an object.

BACKGROUND

An X-ray inspection system includes an X-ray source and a corresponding detector, with the inspected object being between the source and the detector. Collimated X-ray beams pass through the object and arrive at the detector. The magnitude of signals outputted from the detector represents the intensity of the X-ray beams arriving at the detector. The signals are converted to digital image about the inspected object.

The X-rays interact with an object primarily through three effects including photoelectric effect, Compton effect, and electron pair effect. The cross-section of the photoelectric effect is proportional to about the fourth or fifth power of the atomic number of an object. The cross-section of the Compton effect is generally proportional to about the effective atomic number $Z_{eff}$ of the object. The generally interaction cross-section of the electron pair effect is proportional to about a square of the $Z_{eff}$ of the object.

When the energy of the X-rays is lower than 0.5 MeV, the photoelectric effect dominates or has a larger interaction cross-section. At this time, the mass attenuation coefficient of each object is highly correlated with its $Z_{eff}$. As the energy of the X-rays increases to around 1 MeV, the Compton effect becomes dominant. At this time, the correlation between the mass attenuation coefficient of each object and its $Z_{eff}$ becomes weak. When the energy of the X-rays is higher than about 1.02 MeV, the electron pair effect occurs. The interaction cross-section of the electron pair effect increases as the energy of the X-rays becomes higher. Accordingly, the correlation between the mass attenuation coefficient of each object and its $Z_{eff}$ grows stronger.

Then it is possible to obtain information of an object's $Z_{eff}$ by using two sets of X-ray beams of different energy levels to detect the object, and analyzing signals from the two sets of X-ray beams. The X-ray beams having an energy level at the order of MeV are required for detecting an object of a large mass thickness. In the object identification using high-energy dual-energy X-ray beams, the detected object's mass attenuation coefficient and its $Z_{eff}$ are less correlated with respect to X-ray beams of lower energy (e.g., about 1 MeV), while the correlation becomes stronger with respect to X-ray beams of high energy (e.g., about 6 MeV). Information of the detected object's $Z_{eff}$ can be obtained by analyzing signals generated in the detector from the two types of X-ray beams having different energy levels. It can be regarded that the method is based on the different interaction cross-section ration between the Compton effect and pair effect for those materials with different $Z_{eff}$.

Currently, an electron accelerator is often used as X-ray source in X-ray inspection at the MeV energy level. In the electron accelerator, beams of electrons accelerated to the MeV energy level bombard a heavy metal target, and incurs bremsstrahlung that generates X-ray. The typical energy distribution of such X-ray beams ranges from 0 to the energy of electron beam, popularly with the peak at around 0.4 MeV. Its average energy generally in the range of 1.2 to 2 MeV increases with the electron beam energy of the accelerator. In the $Z_{eff}$ discrimination practice of employing double X-ray beams from different energy accelerator, the lower-energy component (i.e, below 0.5 MeV) of those X-ray beams may worsen the object identification due to the photoelectric effect. A flat called by filtering sheet is often employed to reduce the number of photons of the lower-energy X-rays to improve the final $Z_{eff}$ discrimination, however, the result is seriously limited for it also give some reduction on higher-energy photon's number at the same time.

SUMMARY

Methods and apparatuses for measuring an effective atomic number $Z_{eff}$ of an object are provided in view of one or more problems with the conventional technologies.

According to an embodiment, an apparatus for measuring an effective atomic number of an object is provided. The apparatus includes: a ray source configured to product a first X-ray beam having a first energy and a second X-ray beam having a second energy; a Cherenkov detector configured to receive the first X-ray beam and the second X-ray beam that pass through an object under detection, and to generate a first detection value and a second detection value; and a data processing device configured to obtain an effective atomic number of the object based on the first detection value and the second detection value.

According to a further embodiment, a method for measuring an effective atomic number of an object is provided. The method includes: producing a first X-ray beam having a first energy and a second X-ray beam having a second energy; receiving, by a Cherenkov detector, the first X-ray beam and the second X-ray beam that pass through an object under detection, and generating a first detection value and a second detection value; and obtaining an effective atomic number of the object based on the first detection value and the second detection value.

In the above solutions, the Cherenkov detector can eliminate disturbance of X-rays below certain energy threshold with respect to the object identification. In this way, accuracy can be improved for object identification.

BRIEF DESCRIPTION OF THE DRAWINGS

Embodiments of the present invention will be detailed in connection with figures. The above and other objects, features and advantages of the present invention will be more apparent. Throughout the figures, like reference numbers refer to like structure elements. In the figures.

DETAILED DESCRIPTION OF THE EMBODIMENTS

In the following, embodiments of the present invention will be detailed. To be noted, the described embodiments are just intended for illustrating other than limiting the present invention. Numerous specific details are illustrated for a clear and thorough understanding of the present invention. It is apparent to those skilled in the art that these specific details are not necessary for implementation of the present invention. Detailed description of known circuits, materials or methods are omitted which otherwise may obscure the present invention.

Throughout the specification, reference to "an embodiment," "embodiments," "an example" or "examples" means that particular features, structures or characteristics described in connection with such embodiment or example are contained in at least one embodiment of the present invention. The phrase "an embodiment," "embodiments," "an example" or "examples" in various places throughout the specification does not necessarily refer to the same embodiment or example. Further, the particular features, structures or characteristics may be contained in one or more embodiments or examples in any appropriate combination and/or sub-combination. Those skilled in the art will appreciate that the figures are provided here for the purpose of illustration, and may not be drawn to scale.

According to an embodiment of the present invention, a Cherenkov detector is used to detect dual-energy X-rays, in order to measure an effective atomic number of an object under detection and thus identify the object. The Cherenkov detector is a threshold-type detector. When a charged ion travels in a transparent medium at a speed faster than the speed of light in the medium, Cherenkov radiation will occur, thereby generating Cherenkov light. The Cherenkov light may be converted into electric signals with a photodetector. In this way, detection values may be obtained representing the intensity of X-rays that pass through the object under detection.

Generally, X-rays of higher energy will generate secondary electrons with higher energy in the Compton Effect. When the secondary electrons travel at a speed higher than a required threshold, Cherenkov radiation occurs. Therefore, there is a threshold requirement on incident X-rays. Materials (e.g., quartz) selected as a radiator may have a suitable refractivity, density and transparency, such that almost no Cherenkov radiation can occur in the radiator with respect to X-ray photons of lower energy (e.g., 0.5 MeV). Then identification of an object's effective atomic number can be enabled by using a combination of the Cherenkov detector and the dual-energy X-ray source, without adjustment on the energy composition of the X-ray source.

Figure 1:
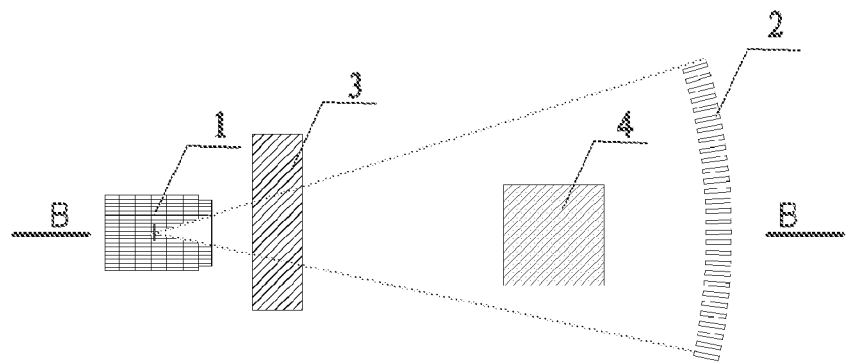
FIG. 1 is a schematic block diagram showing an apparatus for measuring an effective atomic number $Z_{eff}$ of an object using a Cherenkov detector according to an embodiment of the present invention, and is a sectional view along line A-A of FIG. 2.
Figure 2:
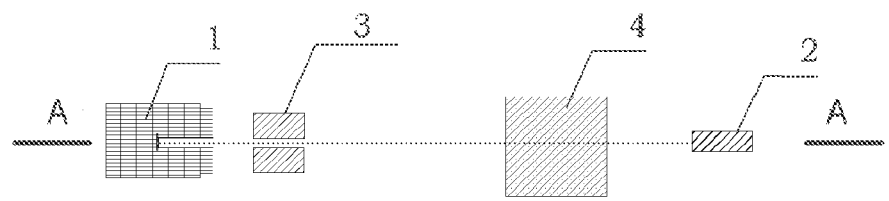
FIG. 2 is a sectional view along line B-B of FIG. 1.

FIG. 1 is a schematic block diagram showing an apparatus for measuring an effective atomic number of an object using a Cherenkov detector according to an embodiment of the present invention, and is a sectional view along line A-A of FIG. 2.

As shown in FIGS. 1 and 2, the apparatus for measuring an effective atomic number of an object using a Cherenkov detector and high-energy dual-energy X-rays may include a dual-energy electron accelerator 1, a Cherenkov detector 2, and an auxiliary circuit connected to the Cherenkov detector 2, such as a data conversion circuit and a data processing device (not shown). The inspected object 4 placed between the Cherenkov detector 2 and the dual-energy electron accelerator 1. The dual-energy electron accelerator 1 may produce high- and low-energy X-ray beams in an alternate manner. The X-ray beams pass through a collimator 3 and then irradiate an object 4 under detection. The Cherenkov detector 2 may receive X-ray beams that pass through the object 4. With the high-energy X-ray beams incident into the Cherenkov detector 2, a first electric signal is generated, for example, representing a first detection value. With the low-energy X-ray beams incident into the Cherenkov detector 2, a second electric signal is generated, for example, representing a second detection value. The data processing device may calculate the object's effective atomic number based on the first and second detection values.

According to an embodiment of the present invention, the dual-energy electron accelerator 1 may produce the low- and high-energy X-ray beams by generating electron beams of different energy levels and bombarding a target with the electron beams.

Figure 3:
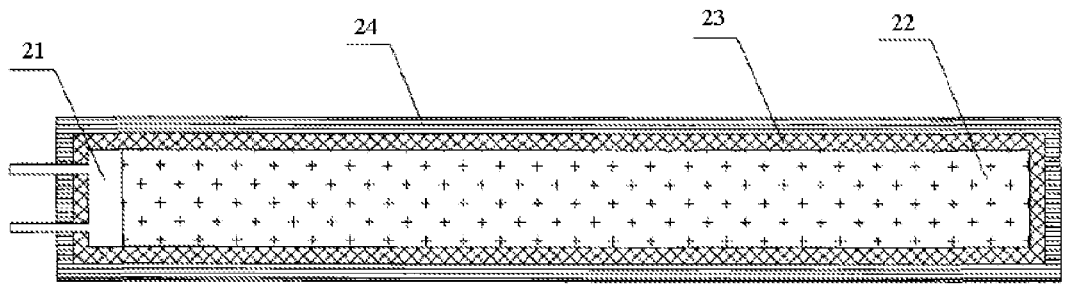
FIG. 3 is a schematic diagram of a Cherenkov detector according to an embodiment of the present invention.

FIG. 3 is a schematic diagram of a Cherenkov detector 2 according to an embodiment of the present invention. The Cherenkov detector 2 shown in FIG. 3 includes a radiator 22 and a photoelectric detection element 21. The surface of the radiator 22 is covered with a sheet of reflector 23 and a light-proof layer 24. The photoelectric detection element 21 is arranged at an end of the radiator 22. X-ray beams enter at the other end of the radiator 22, and generate Cherenkov light while passing through the radiator 22. The surface of the photoelectric detection element 21 that receives the Cherenkov light is perpendicular to the incident X-ray beams. The photoelectric detection element 21 converts the received Cherenkov light into electric signals.

In the Cherenkov detector 2 as shown in FIG. 3, the photoelectric detection element 21 is susceptible to nuclear count effect. The nuclear count effect relates to signals directly produced from rays in a photosensitive device, other than from radiating light or the Cherenkov light within a sensitive volume of the Cherenkov detector 2. Such signals are produced in a manner substantially similar to that of a semiconductor detector for radiation detections. For example, x-rays or secondary electrons generated therefrom may directly produce electron-hole pairs in the sensitive area of a photoelectric diode, other than producing from radiating light or the Cherenkov light. Comparing to Cherenkov effect, Such an event has a very low possibility to happen, but will have significant influence once it occurs. The reason is that generation of one electron-hole pair in a silicon semiconductor requires energy accumulation of only 3.6 eV, and the resulting signal will be superimposed, as disturbing signal, on a signal generated from the Cherenkov light.

Figure 4A:
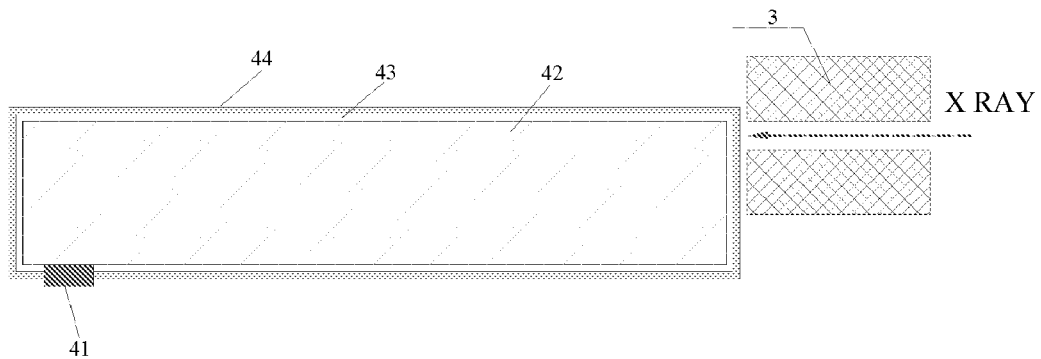
FIGS. 4A and 4B are schematic diagrams of a Cherenkov detector according to other embodiments of the present invention.

According to another embodiment of the present invention, a Cherenkov detector 2 as shown in FIG. 4A is provided to reduce the nuclear count effect. As shown in FIG. 4A, the Cherenkov detector 2 is a detector in a rectangular shape, and includes a radiator 42, a reflective sheet 43 and a light-proof layer 44. X-rays pass through a collimator 3, and then enter the Cherenkov detector 2 along a direction of the length of the Cherenkov detector 2. A photodetector 41, such as a photodiode-, is arranged far away from where the X-rays enter. The surface of the photodetector 41 that receives the Cherenkov light is approximately parallel to the incident direction of the X-rays. According to a further embodiment of the present invention, the Cherenkov detector 2 is in the shape of a rectangular plate having a length of about 250 mm, a width of about 50 mm, and a height of about 10 mm. The direction of the length is the incident direction of the X-ray. Such configuration of the Cherenkov detector 2 can considerably suppress the nuclear count effect. According to a further embodiment of the present invention, the radiator 42 has a cuboid shape, and receives the incident X-ray beams at one of its end surfaces. A photodetector 41 is provided on at least one end surface perpendicular to the end surface receiving the incident X-ray beams. The photodetector 41 receives the Cherenkov light. According to a still further embodiment of the present invention, the side surface of the photodetector 41 that receives the Cherenkov light may surround the radiator 42. This improves efficiency for light collection.

According to a further embodiment of the present invention, the radiator 42 includes a first part, and a second part that is coupled and perpendicular to the first part. The photodetector 41 is disposed at an end of the first part. The x-ray beams enter the second part in a direction approximately parallel to the second part.

Figure 4B:
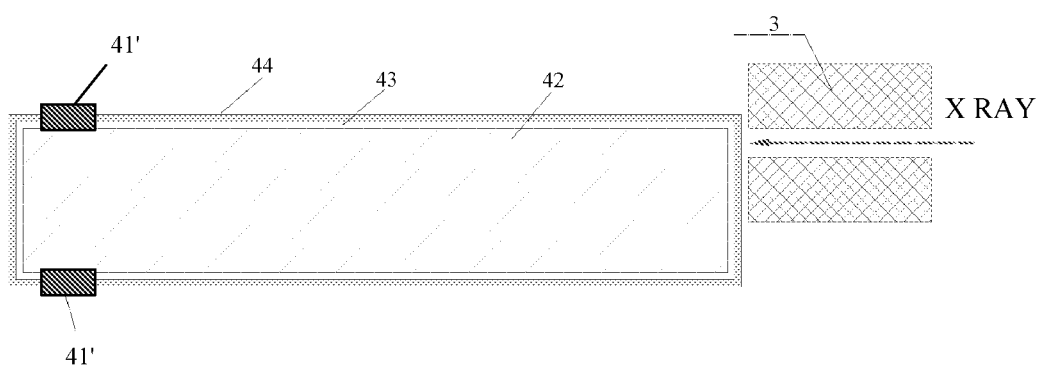

According to a further embodiment of the present invention, the radiator 42 is in a shape of a column. The x-ray beams are received at an end surface of the column. The photodetector 41' is disposed at a side surface of the column for receiving the Cherenkov light. Preferably, the side surface of the photodetector 41' that receives the Cherenkov light may surround the radiator 42, as shown in FIG. 4B. This improves efficiency for light collection.

Figure 5:
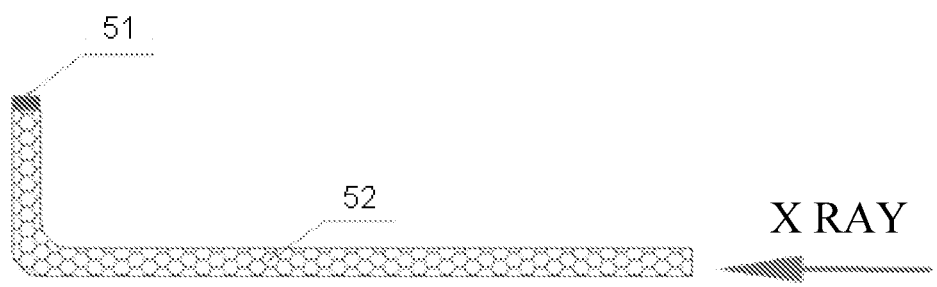
FIG. 5 is a schematic diagram of a Cherenkov detector according to a further embodiment of the present invention.

FIG. 5 is a schematic diagram of a Cherenkov detector 2 according to a further embodiment of the present invention. As shown in FIG. 5, the Cherenkov detector 2 has an "L" shape. A photodetector 51 is provided at an end of one branch of an "L" shaped radiator 52. X-ray beams enter the radiator 52 in a direction approximately parallel to the other branch of the "L" shaped radiator 52.

As shown in FIG. 5, the Cherenkov light enters the "L" shaped radiator 52 from one of its end surfaces. The photodetector 51 is provided at the other end surface of the "L" shaped radiator 52. The surface of the photodetector 51 that receives the X-ray beams is approximately parallel to the incident direction of the X-ray beams.

Figure 6:
FIG. 6 is a schematic diagram showing another application of the Cherenkov detector shown in FIG. 5.

FIG. 6 is a schematic diagram showing another application of the Cherenkov detector 2 shown in FIG. 5. As shown in FIG. 6, Cherenkov light irradiates along a direction opposite to one of the end surfaces of the "L" shaped radiator 52. The photodetector 51 is provided at the other end surface of the "L" shaped radiator 52. The surface of the photodetector 51 that receives the X-ray beams is approximately parallel to the incident direction of the X-ray beams.

Figure 7:
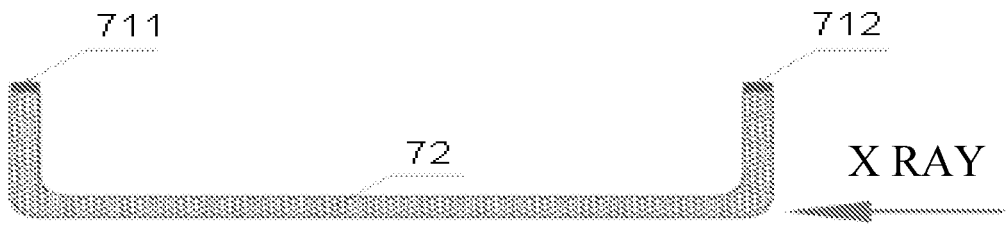
FIG. 7 is a schematic diagram of a Cherenkov detector according to a still further embodiment of the present invention.

FIG. 7 is a schematic diagram of a Cherenkov detector 2 according to a still further embodiment of the present invention. As shown in FIG. 7, the radiator 72 is in a "U" shape, and first and second photodetectors 711 and 712 are provided at both ends of the "U" shaped radiator 72, respectively. X-ray beams enter the bottom of the "U" shaped radiator 72 in a direction approximately perpendicular to the two branches of the "U" shaped radiator 72. This embodiment is useful for efficient collection of Cherenkov light. The Cherenkov detectors 2 in the above embodiments can suppress the nuclear count effect. No matter where the X-rays incident into the sensitive volume of the Cherenkov detector 2 may work, collection of the generated Cherenkov light will remain substantially the same.

To further suppress influence of scattering on the photodetector, the Cherenkov radiator maybe surrounded by a metal layer. The Al layer may absorb X-rays beyond the width of the radiator, and X-rays scattered by the radiator, thereby reducing the intense of a scattering field around the photodetector. Since the atomic number of Al is similar to and less than that of silicon constituting the to material of the photoelectric diode, x-rays sensitive to the material, silicon, can be shielded out by surrounding the photoelectric diode with the Al sheet. According to an embodiment of the present invention, a detector of energy-deposit type may be provided in parallel to the Cherenkov detector 2 and configured for conventional x-ray detection.

As will be appreciated by those skilled in the art, the above-described solutions encompass various technologies such as X-ray inspection systems of direct penetrating detection type, CT detection, and dual-energy CT detection.

The present invention has been described with reference to several exemplary embodiments. It will be appreciated that the terms used here are for illustration, are exemplary other than limiting. The present invention can be practiced in various forms within the spirit or subject matter of the present invention. It will be appreciated that the foregoing embodiments are not limited to any of the above detailed description, and should be construed in a broad sense within the spirit and scope defined by the appended claims. All changes and variations falling into the scope of the claims or their equivalents should be encompassed by the appended claims.

What is claimed is:

1. An apparatus for measuring an effective atomic number of an object, comprising:
 a ray source configured to product a first X-ray beam having a first energy and a second X-ray beam having a second energy;
 a Cherenkov detector configured to receive the first X-ray beam and the second X-ray beam that pass through an object under detection, and to generate a first detection value and a second detection value; and
 a data processing device configured to obtain an effective atomic number of the object based on the first detection value and the second detection value;
 wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals;
 a surface of the photodetector that receives the Cherenkov light is approximately parallel to an incident direction of the first X-ray beam and second X-ray beam, and
 the radiator comprises a first part and a second part coupled and perpendicular to the first part, wherein the photodetector is provided at an end of the first part, and the first X-ray beam and the second X-ray beam enter the second part in a direction approximately parallel to the second part.

2. The apparatus of claim 1, wherein the ray source comprises an electron accelerator and a target, wherein the electron accelerator is configured to produce electron beams of different energy levels to bombard the target and generate the first x-ray beam and the second x-ray beam.

3. The apparatus of claim 1, wherein the photodetector comprises a photoelectric diode.

4. An apparatus for measuring an effective atomic number of an object, comprising:
   a ray source configured to product a first X-ray beam having a first energy and a second X-ray beam having a second energy;
   a Cherenkov detector configured to receive the first X-ray beam and the second X-ray beam that pass through an object under detection, and to generate a first detection value and a second detection value; and
   a data processing device configured to obtain an effective atomic number of the object based on the first detection value and the second detection value,
   wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals,
   a surface of the photodetector that receives the Cherenkov light is approximately parallel to an incident direction of the first X-ray beam and the second X-ray beam, and
   the radiator comprises an L-shaped radiator, the photodetector is provided at an end of one of branches of the L-shaped radiator, and the first X-ray beam and the second X-ray beam enter the other branch of the L-shaped radiator in a direction approximately parallel to the other branch.

5. An apparatus for measuring an effective atomic number of an object, comprising:
   a ray source configured to product a first X-ray beam having a first energy and a second X-ray beam having a second energy;
   a Cherenkov detector configured to receive the first X-ray beam and the second X-ray beam that pass through an object under detection, and to generate a first detection value and a second detection value; and
   a data processing device configured to obtain an effective atomic number of the object based on the first detection value and the second detection value,
   wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals,
   a surface of the photodetector that receives the Cherenkov light is approximately parallel to an incident direction of the first X-ray beam and the second X-ray beam, and
   the radiator comprises an U-shaped radiator, the photodetector is provided at both ends of the U-shaped radiator, and the first X-ray beam and the second X-ray beam enter the other branch of the U-shaped radiator in a direction approximately perpendicular to two branches of the U-shaped radiator.

6. An apparatus for measuring an effective atomic number of an object, comprising:
   a ray source configured to product a first X-ray beam having a first energy and a second X-ray beam having a second energy;
   a Cherenkov detector configured to receive the first X-ray beam and the second X-ray beam that pass through an object under detection, and to generate a first detection value and a second detection value; and
   a data processing device configured to obtain an effective atomic number of the object based on the first detection value and the second detection value,
   wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals,
   a surface of the photodetector that receives the Cherenkov light is approximately parallel to an incident direction of the first X-ray beam and the second X-ray beam,
   the radiator comprises a cuboid-shaped radiator, and receives the first X-ray beam and the second X-ray beam at an end surface of the cuboid-shaped radiator,
   the photodetector is provided on at least one surface of the cuboid-shaped radiator that is perpendicular to the end surface, and receives the Cherenkov light, and
   the surface of the photodetector that receives the Cherenkov light surrounds the cuboid-shaped radiator.

7. An apparatus for measuring an effective atomic number of an object, comprising:
   a ray source configured to product a first X-ray beam having a first energy and a second X-ray beam having a second energy;
   a Cherenkov detector configured to receive the first X-ray beam and the second X-ray beam that pass through an object under detection, and to generate a first detection value and a second detection value; and
   a data processing device configured to obtain an effective atomic number of the object based on the first detection value and the second detection value,
   wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals,
   a surface of the photodetector that receives the Cherenkov light is approximately parallel to an incident direction of the first X-ray beam and the second X-ray beam, and
   the radiator comprises a column-shaped radiator, and receives the first X-ray beam and the second X-ray beam at an end of the column-shaped radiator,
   the photodetector is provided on at least one surface of the column-shaped radiator, and receives the Cherenkov light, and
   the surface of the photodetector that receives the Cherenkov light surrounds the column-shaped radiator.

8. A method for measuring an effective atomic number of an object, comprising:
   producing a first X-ray beam having a first energy and a second X-ray beam having a second energy;
   receiving, by a Cherenkov detector, the first X-ray beam and the second X-ray beam that pass through an object under detection, and generating a first detection value and a second detection value; and
   obtaining an effective atomic number of the object based on the first detection value and the second detection value;
   wherein the Cherenkov detector comprises a radiator configured to receive incident first X-ray beam and second X-ray beam and generate Cherenkov light, a photodetector configured to detect the Cherenkov light and generate electric signals, and an auxiliary circuit configured to generate the first detection value and the second detection value based on the electric signals,
a surface of the photodetector that receives the Cherenkov light is approximately parallel to an incident direction of the first X-ray beam and the second X-ray beam, and
the radiator comprises a first part and a second part coupled and perpendicular to the first part, wherein the photodetector is provided at an end of the first part, and the first X-ray beam and the second X-ray beam enter the second part in a direction approximately parallel to the second part.

* * * * *